US010959780B2

(12) United States Patent
Dumenil et al.

(10) Patent No.: US 10,959,780 B2
(45) Date of Patent: Mar. 30, 2021

(54) METHOD AND SYSTEM FOR HELPING TO GUIDE AN ENDOVASCULAR TOOL IN VASCULAR STRUCTURES

(71) Applicant: THERENVA, Rennes (FR)

(72) Inventors: Aurelien Dumenil, Tergnier (FR); Cemil Goksu, Rennes (FR); Florent Lalys, Rennes (FR); Antoine Lucas, Acigne (FR)

(73) Assignee: THERENVA, Rennes (FR)

( * ) Notice: Subject to any disclaimer, the term of this patent is extended or adjusted under 35 U.S.C. 154(b) by 632 days.

(21) Appl. No.: 15/737,544

(22) PCT Filed: Jun. 24, 2016

(86) PCT No.: PCT/EP2016/064681
§ 371 (c)(1),
(2) Date: Dec. 18, 2017

(87) PCT Pub. No.: WO2016/207358
PCT Pub. Date: Dec. 29, 2016

(65) Prior Publication Data
US 2018/0161099 A1 Jun. 14, 2018

(30) Foreign Application Priority Data
Jun. 26, 2015 (FR) ...................................... 1555944

(51) Int. Cl.
*G06T 7/33* (2017.01)
*A61B 34/10* (2016.01)
(Continued)

(52) U.S. Cl.
CPC ................ *A61B 34/10* (2016.02); *A61B 6/12* (2013.01); *A61B 6/463* (2013.01); *A61B 6/466* (2013.01);
(Continued)

(58) Field of Classification Search
CPC ....... A61B 34/10; A61B 6/504; A61B 6/5235; A61B 6/466; A61B 6/463; A61B 6/487;
(Continued)

(56) References Cited

U.S. PATENT DOCUMENTS 6,711,433 B1   3/2004 Geiger et al.
2005/0004454 A1  1/2005 Mitschke et al.
(Continued)

FOREIGN PATENT DOCUMENTS

CN   103415255 A   11/2013
JP   2001149361 A   6/2001
(Continued)

OTHER PUBLICATIONS

English translation of the International Written Opinion dated Sep. 6, 2016, for corresponding International Application No. PCT/EP2016/064681, filed Jun. 24, 2016.
(Continued)

*Primary Examiner* — Bo Joseph Peng
(74) *Attorney, Agent, or Firm* — David D. Brush; Westman, Champlin & Koehler, P.A.

(57) ABSTRACT

A method and a system are provided for helping to guide an endovascular tool in vascular structures. The method includes an initial planning phase in which a first three-dimensional anatomical model specific to the patient is determined from an acquired three-dimensional image, and an intervention phase in which a final transformation, which is a combination of a rigid transformation and of an elastic transformation, is applied to the first three-dimensional anatomical model specific to the patient in order to obtain a second three-dimensional model specific to the patient. The rigid transformation is estimated between the preoperative three-dimensional image and one or more perioperative two-dimensional images of perioperative two-dimensional
(Continued)

images, and the elastic transformation is calculated as a function of a simulation of vascular deformations that are induced by introducing the tool into the target vascular structure.

11 Claims, 4 Drawing Sheets

(51) Int. Cl.
| | |
|---|---|
| *A61B 6/00* | (2006.01) |
| *A61B 6/12* | (2006.01) |
| *G06T 19/20* | (2011.01) |
| *G06T 17/10* | (2006.01) |
| *A61B 90/00* | (2016.01) |
| *A61B 6/03* | (2006.01) |
| *G06T 3/00* | (2006.01) |
| *G06T 17/00* | (2006.01) |

(52) U.S. Cl.
CPC .............. *A61B 6/481* (2013.01); *A61B 6/487* (2013.01); *A61B 6/488* (2013.01); *A61B 6/504* (2013.01); *A61B 6/5235* (2013.01); *G06T 7/33* (2017.01); *G06T 17/10* (2013.01); *G06T 19/20* (2013.01); *A61B 6/032* (2013.01); *A61B 2034/101* (2016.02); *A61B 2034/105* (2016.02); *A61B 2090/065* (2016.02); *A61B 2090/364* (2016.02); *A61B 2090/374* (2016.02); *A61B 2090/376* (2016.02); *A61B 2090/3764* (2016.02); *G06T 3/00* (2013.01); *G06T 3/0056* (2013.01); *G06T 3/0068* (2013.01); *G06T 17/00* (2013.01); *G06T 2200/08* (2013.01); *G06T 2207/10081* (2013.01); *G06T 2207/10116* (2013.01); *G06T 2207/10121* (2013.01); *G06T 2207/30101* (2013.01); *G06T 2219/2021* (2013.01)

(58) Field of Classification Search
CPC .......... A61B 6/12; A61B 6/481; A61B 6/488; A61B 2034/101; A61B 2034/105; A61B 2090/065; A61B 2090/374; A61B 2090/3764; A61B 6/032; A61B 2090/364; A61B 2090/376; G06T 17/10; G06T 19/20; G06T 7/33; G06T 2219/2021; G06T 2200/08; G06T 3/0056; G06T 3/0068; G06T 17/00; G06T 3/00; G06T 2207/10116; G06T 2207/10081; G06T 2207/10121; G06T 2207/30101; G06T 2090/364

See application file for complete search history.

(56) References Cited

U.S. PATENT DOCUMENTS

| | | | |
|---|---|---|---|
| 2009/0088830 A1 | 4/2009 | Mohamed et al. | |
| 2013/0094742 A1* | 4/2013 | Feilkas | A61B 6/584 382/131 |
| 2013/0303893 A1 | 11/2013 | Duindam et al. | |
| 2014/0044333 A1* | 2/2014 | Barth, Jr. | G06T 7/33 382/131 |
| 2014/0073907 A1* | 3/2014 | Kumar | A61B 10/0241 600/414 |
| 2016/0038252 A1* | 2/2016 | Barth, Jr. | A61B 34/25 600/424 |
| 2016/0078633 A1* | 3/2016 | Tahmasebi Maraghoosh | G06K 9/46 382/131 |
| 2017/0202633 A1* | 7/2017 | Liu | A61B 90/00 |
| 2017/0337682 A1* | 11/2017 | Liao | G06T 7/30 |
| 2018/0104010 A1* | 4/2018 | Miga | G06T 7/33 |
| 2018/0368917 A1* | 12/2018 | Dekel | A61B 34/20 |
| 2019/0365475 A1* | 12/2019 | Krishnaswamy | A61B 17/3403 |
| 2020/0163584 A1 | 5/2020 | Barley et al. | |

FOREIGN PATENT DOCUMENTS

| | | |
|---|---|---|
| JP | 2014509239 A | 4/2014 |
| WO | 03088143 A2 | 10/2003 |
| WO | 2008087629 A2 | 7/2008 |
| WO | 2011128797 A1 | 10/2011 |
| WO | 2012114224 A1 | 8/2012 |

OTHER PUBLICATIONS

International Search Report dated Sep. 6, 2016, for corresponding International Application No. PCT/EP2016/064681, filed Jun. 24, 2016.
Chinese Office Action with English translation dated Apr. 26, 2020 for corresponding Chinese Application No.201680044571.2.
Japanese Notice of Reasons for Rejection with English translation, dated Feb. 12, 2020, for corresponding Japanese Application No. 2018-518787.

* cited by examiner

METHOD AND SYSTEM FOR HELPING TO GUIDE AN ENDOVASCULAR TOOL IN VASCULAR STRUCTURES

CROSS-REFERENCE TO RELATED APPLICATIONS

This Application is a Section 371 National Stage Application of International Application No. PCT/EP2016/064681, filed Jun. 24, 2016, the content of which is incorporated herein by reference in its entirety, and published as WO 2016/207358 on Dec. 29, 2016, not in English.

FIELD OF THE DISCLOSURE

This invention relates to a method for helping to guide an endovascular tool in vascular structures, and an associated system.

It has application in the field of image-guided endovascular interventions.

BACKGROUND OF THE DISCLOSURE

Endovascular interventions make it possible to treat vascular diseases in a minimally invasive manner. They generally consist in inserting by endovascular route a medical device with the purpose of interacting with the pathological tissues. Endovascular interventions are in particular used to treat aortic aneurysms as well as stenosis and arterial thrombosis, via the introduction of various suitable endovascular tools such as a balloon or a stent.

Contrary to conventional surgical interventions that require making a wide opening in the body of the patient in order to access the tissues of interest, endovascular interventions require only fine incisions in order to be able to insert the tools into the vascular structure. They have several advantages, in particular an increase in the short-term success rate as well as a decrease in perioperative morbidity and in the length of hospital stay. Despite the generalisation of these interventions, they remain delicate and have to be secured and made dependable. Access to the pathological tissues is made difficult by the nature of the intervention. The manipulation and the control of the instruments require substantial precision in order to favour the success of the treatment. Moreover, the following of operating procedures can be carried out only through the intermediary of perioperative imaging.

In the field of endovascular interventions two-dimensional image acquired by fluoroscopy are used, making it possible to guide the insertion of medical devices, such as catheters, into the femoral artery and into other vascular branches.

Fluoroscopy designates a medical imaging technique that makes it possible to view anatomical structures in motion and in real time. As arteries are soft tissues and therefore invisible to X-rays, a radiopaque contrast agent can be administered to the patient in order to bring out the vascular structure by indicating the pathway of the arteries.

The two-dimensional images are acquired and used during an operating phase, therefore an intervention phase.

In order to improve the assistance provided during the operating phase, it has been proposed to also use three-dimensional image data (or 3D images), acquired during a preoperative phase or planning phase, obtained by acquisition techniques such as for example tomography also called CT for "computed tomography", magnetic resonance imaging (MRI)). Indeed, very often, the two-dimensional information concerning the organs is not sufficient and the operations require three-dimensional knowledge. These 3D images are acquired before the operation for the diagnosis of the disease or for observing the shape of the aneurysm and preparing the intervention, and are therefore easily available during the operation.

Using three-dimensional information generated in the preoperative phase during perioperative navigation requires a putting into correspondence of this information with the two-dimensional imaging (2D) acquired during the intervention phase. The putting into correspondence is carried out thanks to a recalibration process that makes it possible to express the various data in the same spatial reference.

The objective is to view, at the same time and on the same image, various types of information such as images of different modalities or of previously extracted anatomical models. This makes it possible to provide the practitioner with additional information as well as a better understanding of the operating field, allowing him to improve the precision of the intervention and to secure the operating procedure.

There are surgical systems that are image guided intended for so-called hybrid operating rooms, provided with a support device for an image acquisition device able to rotate around the patient for the acquisition of images, for example via X-ray. Such a support device known under the name rotational motorised C-arm, is used in rotational angiography. Using such a device makes it possible to acquire three-dimensional image data during the intervention and to facilitate the merger between image data acquired previously and image data acquired during the intervention, via a 3D/3D recalibration. The updating of the recalibration is then fully automated, and the operator can easily change the angles of the C-arm or move the table of the patient without calling the image merger into question. In the end, the quantity of contrast agent to be injected is less and the duration of radiation is reduced.

However, using a motorised rotating C-arm is not practical in an operating room, and can hinder the movement of the practitioner. In addition, such equipment is expensive and many hospitals cannot be equipped with it.

In most cases, operating rooms are equipped with a conventional mobile and non-motorised C-arm, which is a lighter and less expensive piece of equipment. The objectives of assistance are the same as with the motorised C-arms, but the image merger is no longer fully automated. In this case, the recalibration is carried out between the 3D image acquired in the preoperative phase and the 2D images acquired during the operation, and the recalibration has to be updated every time the patient, table or C-arm moves.

In addition, the 2D images acquired during the operating phase, also called perioperative images, contain various content that makes the recalibration difficult. Indeed, these images contain anatomical structures of different types: constantly visible bone structures, vascular structures, which are fully or partially revealed thanks to the contrast agents injected, as well as endovascular tools, for example catheters, flexible or rigid guides, or stent delivery devices. Consequently, it is generally difficult to determine the geometrical transformation between the preoperative image data and the perioperative image data.

In addition, the anatomical structures undergo deformations between the preoperative phase of acquiring 3D image data and the intervention phase, with these deformations able to be caused on the one hand by physiological changes, but especially by the introduction of endovascular tools into the vascular structures of the patient. In particular, the vascular structure is deformed by the introduction of a rigid guide, which has for purpose to facilitate the insertion afterwards of a stent delivery system.

SUMMARY

The invention has for object to overcome the disadvantages of known methods, in order to improve image-guided endovascular interventions by allowing for a better taking of the deformations of the vascular structures of the patient into account in the intervention phase.

To this effect, the invention proposes a method for helping to guide an endovascular tool in vascular structures. This method comprises the steps of:
  during an initial planning phase,
    obtaining and memorising a preoperative three-dimensional image comprising a target vascular structure of a patient,
    determining a first three-dimensional anatomical model specific to the patient from the three-dimensional image acquired, this first three-dimensional anatomical model being located in the same spatial reference as the three-dimensional image,
  during an intervention phase,
    acquiring one or several perioperative two-dimensional images comprising the target vascular structure of the patient, opacified or not,
    estimating a rigid transformation between the preoperative three-dimensional image and the perioperative two-dimensional images,
    estimating an elastic transformation between said three-dimensional image and the two-dimensional images according to the rigid transformation and of a simulation of vascular deformations induced by introducing the tool into the target vascular structure,
    applying a final transformation, a combination of the rigid transformation and of the elastic transformation, to the first three-dimensional anatomical model specific to the patient in order to obtain a second three-dimensional model specific to the patient,
    displaying said second three-dimensional model specific to the patient as superposition on the two-dimensional images acquired.

Advantageously, the method of the invention comprises a combination of a rigid transformation and of an elastic transformation, making it possible to generate a second three-dimensional model of the target vascular structures which is deformed in coherence with the deformations of these structures during the intervention phase. As such, the second three-dimensional model is displayed in superposition of the two-dimensional images acquired in a context updated in relation to the anatomy of the patient, which makes it possible to improve the assistance provided during a minimally invasive endovascular intervention.

The method according to the invention can also have one or several of the characteristics herein below, taken independently or in combination.

The step of estimating an elastic transformation comprises a modelling of the vascular structures of the patient from the preoperative three-dimensional image acquired.

The step of estimating an elastic transformation comprises the constructing of a biomechanical interaction model between the vascular structures and the endovascular tool.

The method comprises a simulation of the interaction between the endovascular tool and the target vascular structure carried out by a finite element analysis method.

The estimation of the elastic transformation comprises an additional step of correction that uses said perioperative two-dimensional images.

The step of correction comprises a projection of simulated positions of the endovascular tool on at least one perioperative two-dimensional image taken after the actual introduction of the endovascular tool, and a quantification of the difference between said simulated positions and actual positions of the endovascular tool.

The method further comprises a step of recalibrating between said simulated positions and said actual positions.

The first three-dimensional anatomical model specific to the patient is represented by a structure among a volume, a mesh of points, a set of contours and a set of anatomical markers.

The estimation of a rigid transformation is carried out by automatic, semi-automatic or manual recalibration, between the preoperative three-dimensional image and at least one perioperative two-dimensional image.

According to a second aspect, the invention relates to a system for helping to guide an endovascular tool in vascular structures, characterised in that it comprises an imaging device able to acquire two-dimensional images of portions of the body of a patient, a programmable device and a viewing unit.

The system is adapted for:
  during an initial planning phase,
    obtaining and memorising a preoperative three-dimensional image comprising a target vascular structure of a patient,
    determining a first three-dimensional anatomical model specific to the patient from the three-dimensional image acquired, this first three-dimensional anatomical model being located in the same spatial reference as the three-dimensional image,
  during an intervention phase,
    acquiring one or several perioperative two-dimensional images comprising the target vascular structure of the patient, opacified or not,
    estimating a rigid transformation between the preoperative three-dimensional image and the perioperative two-dimensional images,
    estimating an elastic transformation between said three-dimensional image and the two-dimensional images according to the rigid transformation and of a simulation of vascular deformations induced by introducing the tool into the target vascular structure,
    applying a combination of the rigid transformation and of the elastic transformation to the first three-dimensional anatomical model specific to the patient in order to obtain a second three-dimensional model specific to the patient,
    displaying, on the viewing unit, said second three-dimensional model specific to the patient in superposition on the two-dimensional images acquired.

According to a third aspect, the invention relates to a computer program comprising instructions for implementing the steps of a method for helping to guide an endovascular tool in vascular structures such as described briefly hereinabove, during the execution of the programme by a processor of a programmable device.

BRIEF DESCRIPTION OF THE DRAWINGS

Other characteristics and advantages of the invention shall appear in the description which is given of it herein below, for the purposes of information and in a non-limiting manner, in reference to the annexed figures, among which.

DETAILED DESCRIPTION OF ILLUSTRATIVE EMBODIMENTS

Figure 1:
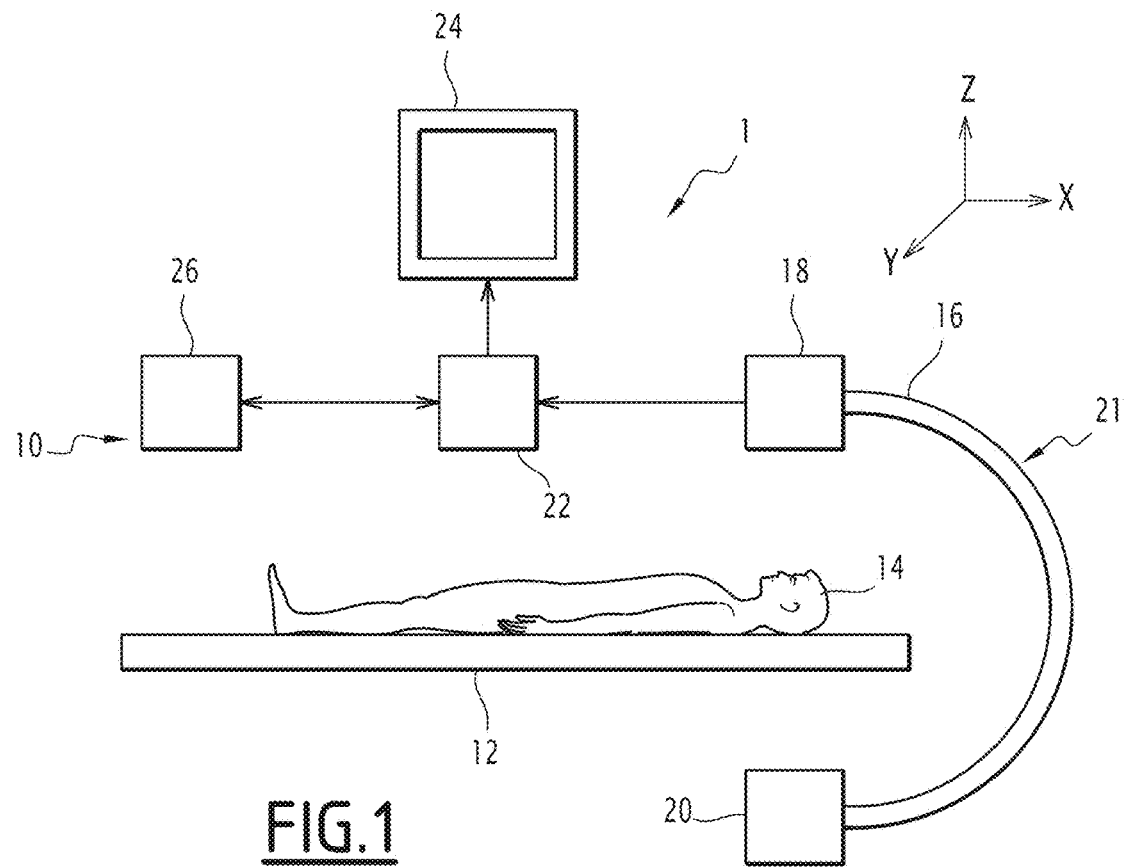
FIG. 1 diagrammatically shows an image-guided endovascular intervention system.

FIG. 1 diagrammatically shows an operating room 1, equipped with an image-guided endovascular intervention system 10.

The operating room 1 is equipped with an operating table 12, whereon is represented a patient 14 to be treated by an endovascular intervention.

The intervention system 10 comprises an X-ray imaging device 21, itself comprised of a support device 16 in the shape of a hoop, a source of X-rays 18 and a unit 20 for receiving and detecting X-rays, positioned facing the source 18. This imaging device is able to capture images of the elements positioned between the source 18 of X-rays and the unit 20 for receiving and detecting, and is also able to rotate about two axes, the X axis and the Y axis according to the needs of the operator.

As such, the imaging device 21 shown is able to capture two-dimensional X-ray images of various portions of the body of the patient, comprising target vascular structures.

The intervention system 10 also comprises a programmable device 22, comprising one or several processors, associated with a viewing unit 24 comprised of one or of several screens and of a man-machine interface 26.

The man-machine interface 26 comprises means of pointing and selecting elements, for example a keyboard-mouse unit, a touchpad, a 3D gesture interface without contact or a combination of these devices.

In an embodiment, the man-machine interface 26 is integrated with the viewing unit 24 in the form of a touch screen.

The programmable device 22 is able to receive the two-dimensional X-ray images acquired by the X-ray imaging device and in processing them according to a method for helping to guide an endovascular tool in vascular structures according to the invention.

The two-dimensional images acquired during the intervention phase are displayed on the viewing unit 24, as well as a three-dimensional model specific to the patient, allowing for a more precise guiding of the endovascular tools in an updated context in relation to the anatomy of the patient.

The endovascular tools are selected from a catheter, an endovascular device of the stent type, a flexible or rigid guide, a catheter, a stent or a balloon.

Figure 2:
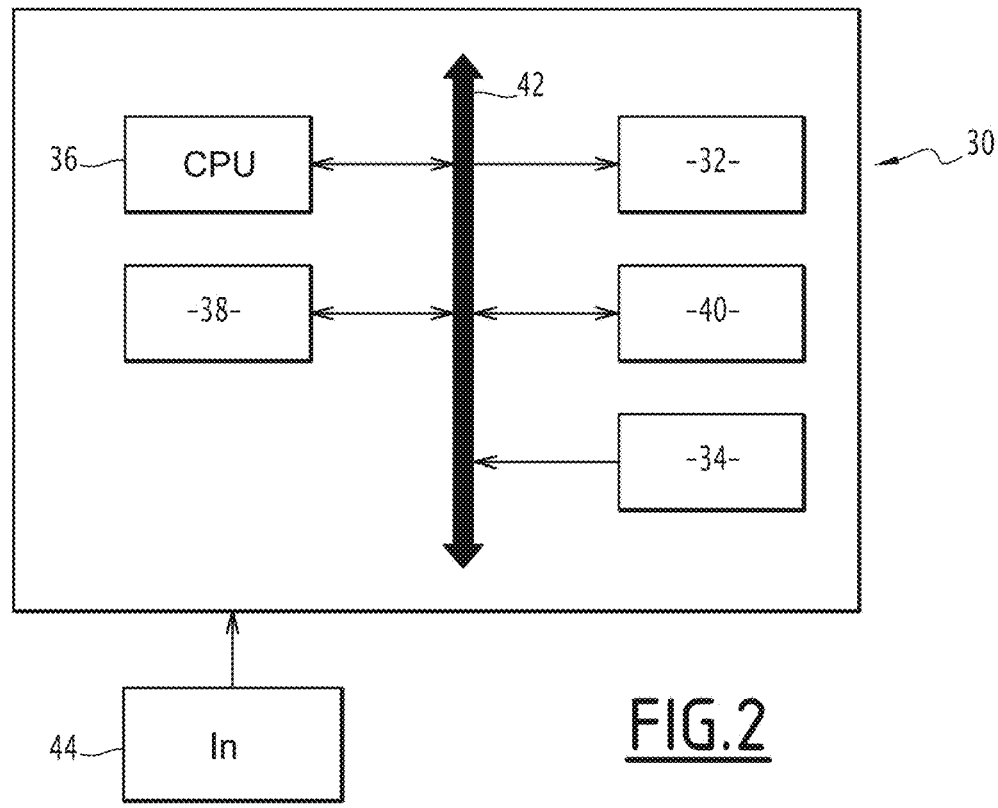
FIG. 2 is a block diagram of the main blocks of a programmable device able to implement the method of the invention.

FIG. 2 shows the main blocks of a programmable device 30 able to implement the method for helping to guide an endovascular tool in vascular structures according to an embodiment of the invention.

A programmable device 30 able to implement the invention, comprises a screen 32, similar to the viewing unit 24, a unit 34 for entering the commands of an operator, for example a keyboard, a mouse, a touchpad or an interface without contact, a central processing unit 36, or CPU, able to execute computer program instructions when the device 30 is turned on. The device 30 optionally comprises a controller 40, which makes it possible to send commands and to select elements remotely.

The device 30 also comprises a unit for storing information 38, for example registers, able to store executable code instructions that allow for the implementing of programs comprising code instructions able to implement the method according to the invention. The various functional blocks of the device 30 described hereinabove are connected via a communication bus 42.

The device 30 is able to receive image data from a source 44.

The method of the invention is adapted to be implemented by a programmable device such as a computer integrated into a standard operating room, which makes it possible to limit the costs of equipment.

Figure 3:
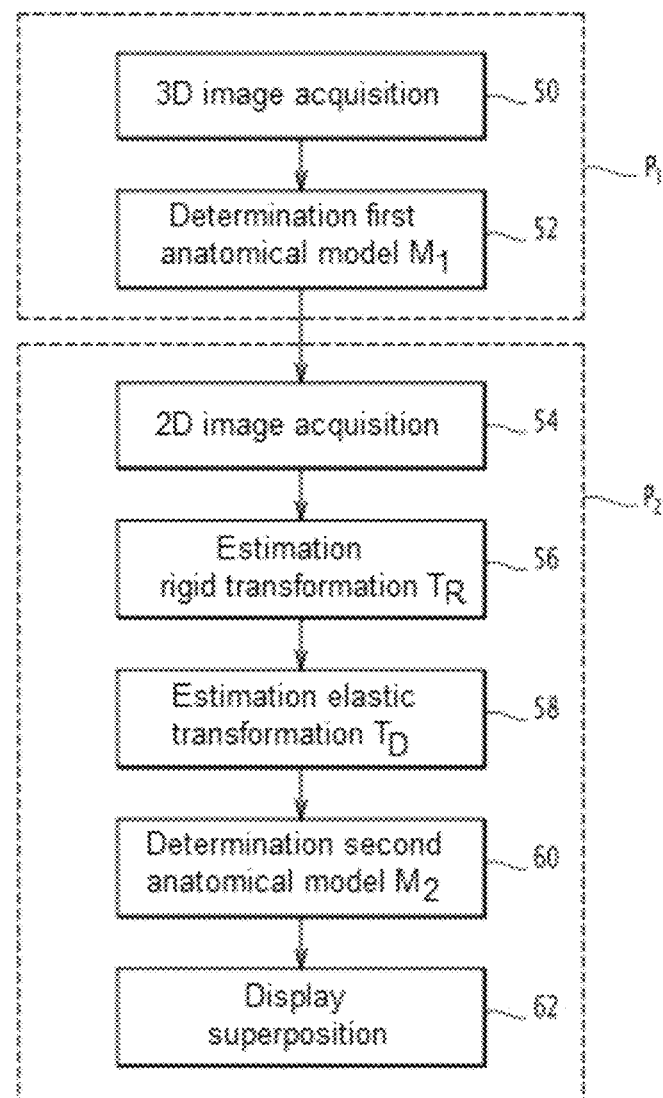
FIG. 3 is a flow chart of a method for helping to guide an endovascular tool according to an embodiment of the invention.

FIG. 3 shows the main steps implemented in a method for helping to guide an endovascular tool in vascular structures according to an embodiment of the invention, implemented by a processor 36 of a programmable device 30.

The method comprises two phases, a preoperative planning phase $P_1$, which is carried out prior to the intervention and of which the results are memorised, and an intervention phase $P_2$, carried out during an intervention of a practitioner on a patient.

In an embodiment shown in FIG. 3, the planning phase $P_1$ comprises the implementing of two steps.

A first step 50 consists in acquiring and in memorising a preoperative 3D image of a portion of the body of the patient comprising a vascular structure to be treated of the patient.

For example, for an abdominal aortic aneurysm, the 3D image acquired contains the abdominal aorta.

For example, the 3D image, also called volume image, is obtained by the tomography technique known under the name of CT.

Alternatively, other known techniques such as the angioscanner or MRI are used.

These techniques for acquiring 3D images are known in the field of medical imaging and are not described in any further detail here.

The preoperative 3D image is memorised in a suitable format in a memory of the programmable device implementing the method of the invention.

Advantageously, the 3D image obtained is representative of the anatomy of the patient to be treated, and makes it possible to take measurements and to size the endovascular tools to be used during the intervention.

The step 50 of acquiring a 3D image of a vascular structure of the patient is followed, in the planning phase $P_1$, by a step 52 of determining a first virtual three-dimensional anatomical model of the patient (model $M_1$) comprising a model of the target vascular structure.

This first virtual three-dimensional anatomical model is obtained by image processing applied to the 3D image, by application of automatic or semi-automatic algorithms.

For example, a semi-automatic segmentation algorithm of the graph section type can be used. This algorithm, which is inexpensive in terms of interaction with the user, offers fast and precise results and makes it possible to obtain a precise segmentation of the aorta and of the renal and internal iliac arteries.

According to the algorithm used, the first virtual three-dimensional anatomical model is represented either in the form of a volume (3D image), a mesh of points, a set of contours, anatomical markers or a combination of these elements. The representation of the first virtual three-dimensional anatomical model is memorised for use in the intervention phase $P_2$.

For example, such a first virtual three-dimensional anatomical model $M_1$ can include the segmented volumes of the aorta, of the internal iliac arteries and of the renal arteries, of the vertebral column as well as calcified plates.

The preoperative planning phase $P_1$ is followed by the intervention phase $P_2$.

During a step 54 of acquiring images in the intervention phase, several perioperative 2D images comprising an anatomical region of interest of the patient are obtained. The anatomical region of interest comprises the target vascular structure, opacified or not by contrast agents.

According to an embodiment, the acquisition of images is carried out by a fluoroscopic X-ray imaging device 21 comprising a support device of the C-arm type such as shown in FIG. 1. These images are obtained in real time and form a video stream. The vascular structures can be rendered temporarily visible thanks to an injected contrast agent.

Alternatively, perioperative 2D images are obtained by a device for acquiring images by ultrasound.

The plurality of perioperative 2D images acquired at the step of acquiring 54 comprises at least one 2D image of the anatomical region of interest.

The step 54 of acquiring perioperative 2D images is followed by a step 56 of estimating a rigid transformation $T_R$ that makes it possible to carry out a spatial recalibration between the preoperative 3D image acquired during the step 50 and the perioperative 2D images acquired during the step 54. The estimated rigid transformation makes it possible to put the structures of interest of each perioperative 2D image into correspondence with those of the preoperative 3D image. The structures of interest include for example bone structures that are constantly visible.

In other terms, this entails estimating a rigid transformation $T_R$ that puts the spatial reference of the 3D image and of the first virtual three-dimensional anatomical model into correspondence with the spatial reference of the images acquired in the operating phase.

According to a first embodiment, the step 56 implements the simultaneous display of the 3D images and of the 2D images acquired, and a manual recalibration, carried out via visual inspection, of several points of interest of the 3D images and of the 2D images inspected.

According to an alternative, an automatic recalibration algorithm is implemented. Note that many 3D/2D recalibration algorithms are known in the field of medical imaging.

For example, an automatic recalibration of the iconic type can be implemented, by using a measurement of similarity based on the difference in gradients between the preoperative 3D image and one or several perioperative 2D images, coupled with an optimisation strategy of the gradient-based descent type or Powell optimiser.

According to another alternative, a semi-automatic recalibration is implemented, wherein the determining of an initial transformation is carried out manually. In this type of method, the manual initialisation makes it possible to have the two images to be recalibrated correspond roughly, and the automatic recalibration is then launched afterwards in order to refine the result.

At the end of the step 56, the values of the parameters that define the estimated rigid transformation are memorised.

Advantageously, the step 56 of determining a rigid transformation can be carried out at various stages of the intervention, for example before the introduction of endovascular tools into the vascular structure of the patient, or after this introduction.

Likewise, the step 56 of determining a rigid transformation can be carried out from one or several perioperative 2D images, acquired with or without injecting a contrast agent, showing the bone structure or the vascular structure, with or without the presence of tools, as well as by using a single angle of incidence of the C-arm or several.

At this stage, the recalibration is not precise enough to allow for a perfect correspondence of the preoperative 3D image with the perioperative 2D images. The step 56 of determining a rigid transformation is therefore followed by a step 58 of estimating an elastic transformation of adjustment $T_D$, which makes it possible to improve the recalibration between the preoperative 3D image and the perioperative 2D images.

The estimation of the elastic transformation is based on a deformation of the anatomical structures due to the introduction of an endovascular tool into the vascular structures of the patient.

It is considered that the tool introduced, for example a guide or a catheter, is the main cause of the deformations, and that the deformations introduced can be modelled by a specific biometric model.

An embodiment of the determination or estimation of an elastic transformation shall be described in more detail hereinafter in reference to FIG. 4.

The step of determining an elastic transformation is followed by a step 60 of combining the rigid transformation $T_R$ and the deformation parameters of the elastic transformation $T_D$ in order to obtain a final transformation $T_F$.

The final geometric transformation makes it possible to put each point of the perioperative 2D images into correspondence with a point or voxel of the space of the preoperative 3D images.

The final geometric transformation is applied to the first virtual three-dimensional anatomical model $M_1$ in order to obtain a second deformed virtual three-dimensional anatomical model $M_2$.

This second three-dimensional anatomical model $M_2$ is more precise as it takes into account the current deformations of the vascular structures during the intervention phase.

For example, the final transformation $T_F$ is applied to all the mesh points defining the model $M_1$ in order to obtain mesh points defining the model $M_2$, and these mesh points defining the model $M_2$ are memorised.

Finally, during a step of displaying 62, the second three-dimensional anatomical model obtained is displayed in superposition with the perioperative 2D images.

The assistance with endovascular navigation and with guiding the introduction of an endovascular tool into the vascular structure of the patient is as such improved, because the anatomical model specific to the patient is more precise and better suited to the perioperative context.

Advantageously, the assistance provided by the displaying of the merger of images therefore makes it possible to secure, make dependable and guide the interventional procedure by the adding of pertinent information extracted in the preoperative phase and added within the operating room. It must make it possible in the long term to reduce the injections of contrast agent and the emissions of X-rays.

Figure 4:
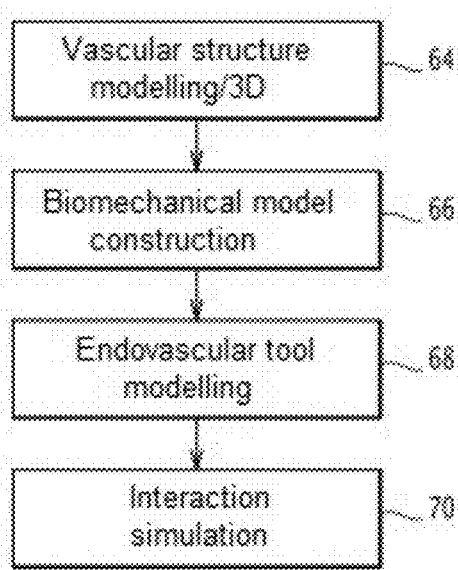
FIG. 4 is a flow chart of the steps of determining an elastic transformation according to an embodiment of the invention.

FIG. 4 shows an embodiment of the step of determining an elastic transformation.

The determination of an elastic transformation comprises a first step 64 of modelling the target vascular structure of the patient carried out from the preoperative data, in particular from memorised 3D images. The modelling consists in creating a geometrical representation of the vascular structure that can be used to estimate the vascular deformations.

In an embodiment, the vascular structure is modelled by B-spline curves corresponding to the contours of the first anatomical model. An interpolation is carried out between the B-spline curves in order to create a surface model that represents the vascular wall.

Then, a step 66 of building a biomechanical model specific to the patient is implemented. It consists in defining the mechanical behaviour of the vascular structure by assigning mechanical properties to the geometrical representation obtained in the step 64. The biomechanical model must take into account the specificities of the patient, namely the local state of the vascular wall (healthy, calcified) and the relation between the vascular structure and its direct environment (interactions with the bone structure and the surrounding soft tissues).

In an embodiment, a simulation of the interactions between the tools and the vascular structure, such as described in reference to the step 70 hereinafter, is carried out for a set of patients referred to as learning. The simulation error is quantified by measuring the difference between the shape of the simulated tools and that of the actual tools that can be observed on one or several perioperative images. The parameters of the biomechanical model that define that relation between the vascular structure and its direct environment are progressively adjusted for the purpose of minimising simulation error.

Expressions connecting preoperative data coming from memorised 3D images with the value of the parameters of the biomechanical model are defined from optimum values obtained at the end of the progressive adjusting of the parameters of the biomechanical model for each patient. These expressions define an adaptive biomechanical model that is entirely defined from the preoperative data coming from memorised 3D images and anatomical and mechanical knowledge.

In an embodiment, the values used for, the rigidity of the tissues come from average data coming from characteristics reported in literature, while the state of calcification of the arteries is taken into account specifically for each patient by assigning a different rigidity to the calcified zones and to the healthy zones that can be distinguished on the preoperative imaging. For the levels of deformation reached during simulations, the anisotropy of the wall can be neglected.

The following step 68 of modelling endovascular tools consists in creating a geometrical representation of the endovascular tools according to their actual shape and in defining a behaviour law according to their mechanical properties.

For example, a rigid guide used in mini-invasive procedures can be modelled by 1D elements of the circular section beam type. For delivery systems, a tubular structure with homogeneous section to which a material with an equivalent rigidity is assigned can be used for the modelling.

In an embodiment, the mechanical properties of the endovascular tools are characterised by means of mechanical tests that make it possible to establish a relation between the force applied to the tool and the deformation of the tool. For example, a 3-point bending test can be carried out in order to quantify the flexural rigidity of the endovascular tools. The properties characterised as such are used in the simulations to represent the actual mechanical behaviour of the tools.

The step of modelling endovascular tools 68 is followed by a step 70 of simulating the interaction of the endovascular tools introduced or to be introduced into the vascular structure with the wall of the vascular structure of the patient.

In an embodiment, the simulation is carried out using a finite element analysis. The geometrical representation of the biomechanical model specific to the patient and of the model of the endovascular tools is discretised into a set of elements having a predetermined shape (triangular shell elements, beam elements, hexahedron elements, etc.).

The mechanical behaviour of each element is defined according to the mechanical behaviour previously attributed to the models of the vascular structure and of the endovascular tools. The interactions between the two models are managed by a contact management method, for example by a method of penalisation.

In an embodiment, the conditions at the limits are defined with regards to the anatomical and mechanical considerations coming from literature and the knowledge of surgeon experts. For example, the proximal and distal ends of the vascular structure are fixed and the link between the vascular structure and the surrounding tissues is modelled by an additional rigidity.

In an embodiment, a vascular pre-stress is applied before simulating the tool/tissues interactions. Its role is to take into account the state of rest of the vascular structure. Before simulating the tool/tissue interactions, the state of pre-tension of the vascular wall due to the presence of the blood pressure is taken into account. For this a geometry corresponding to the state of rest of the vascular structure (zero blood pressure), referred to as "zero-pressure" geometry is determined, then the arterial pressure is applied in this "zero-pressure" geometry in order to tension the vascular wall.

The geometry of the vascular wall is determined in particular by parameters of diameter, length, angulation, thickness.

The reference geometry observed on the preoperative image is chosen as a first estimation of the zero-pressure state, and then is corrected iteratively at each step of the algorithm. For this, each iteration consists in applying the internal pressure in the zero-pressure geometry then in comparing the final geometry obtained as such with the reference geometry. The zero-pressure geometry is then corrected by applying the opposite of the position difference observed.

The simulation of the interaction of the endovascular tools with the wall of the vascular structure of the patient is carried out by initialising the tools inside the vascular structure by imposed constraints, for example of the imposed displacement type, then by observing the vascular deformations caused by the tools when the imposed constraints are progressively cancelled.

The initialisation consists in constraining the tool inside the vessel lumen, for example on a path that minimises its flexural energy. Once inside the vessel lumen, the contact between the internal face of the vascular wall and the tool is activated. Finally the constraints required for the initialisation are progressively released. A mechanical balance will then establish itself between the tool and the vascular structure generating the vascular deformations that are desired to be calculated.

In an alternative embodiment of the simulation, the tools are inserted progressively inside the vascular structure until they are fully inserted. The vascular deformations can be calculated at each sub-step of the progressive insertion.

The steps described hereinabove define an embodiment in order to define the elastic transformation.

In an alternative embodiment, the determining of an elastic transformation comprises an additional step of correlation. This step consists in projecting simulated positions of the tool introduced onto one or several perioperative 2D images, in quantifying the difference between the simulated positions and the actual positions of the actual tool, and in using a recalibration model 2D/2D in order to determine a correction of the elastic transformation. A known 2D/2D recalibration algorithm can be used, such as a recalibration using a geometrical approach.

Figure 5:
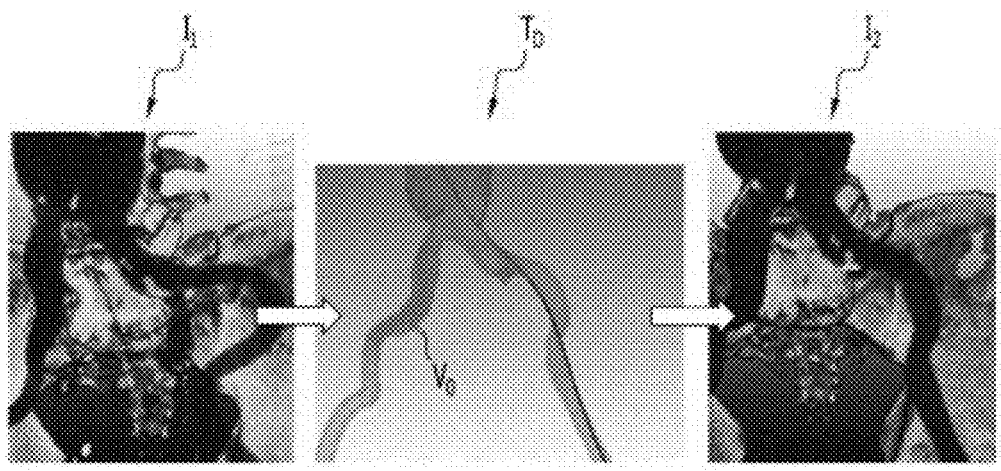
FIG. 5 is an example of images of vascular structures after recalibration.

FIG. 5 shows a vascular structure $V_P$, with the result $I_1$ of the rigid transformation $T_R$ applied to a preoperative 3D image shown as a cross-section, and the result $I_2$ of the final transformation $T_F$, coming from the combination of the rigid transformation and of the elastic transformation, applied to the same preoperative 3D image.

At the centre, the result of the elastic transformation is shown.

Figure 6:
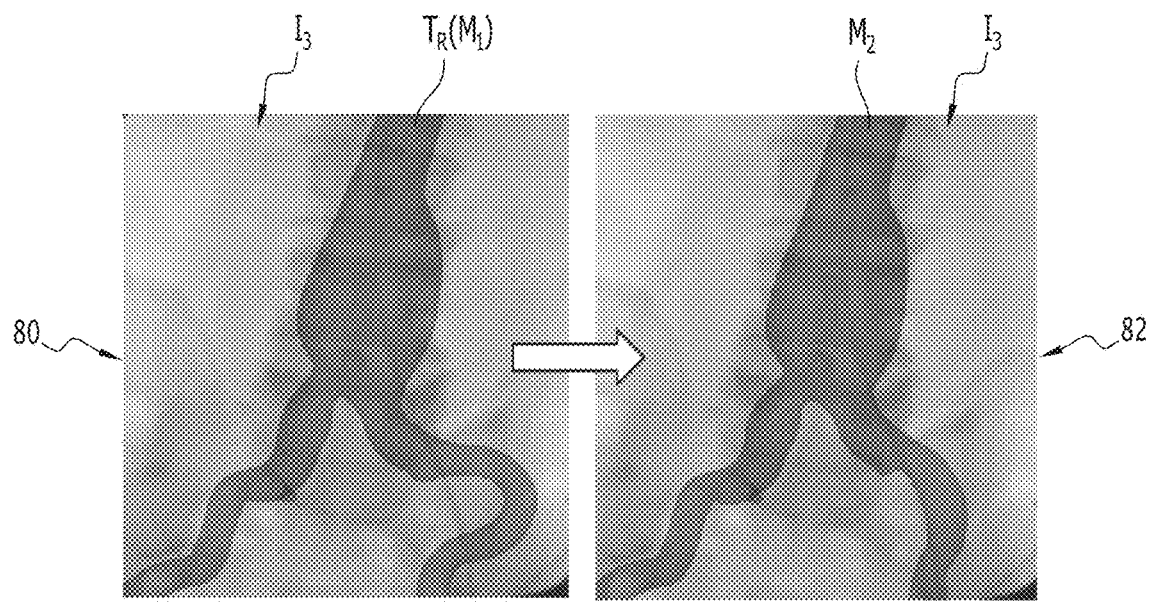
FIG. 6 is an example of a merger of a perioperative 2D image and of an anatomical model before and after application of the elastic transformation.

FIG. 6 diagrammatically shows a merger of a perioperative 2D image $I_3$ and of a three-dimensional anatomical model in order to facilitate the guiding and the navigation of the introduction of an endovascular tool.

In the illustration 80, the rigid transformation $T_R$ of the first three-dimensional anatomical model $M_1$ is projected onto the perioperative image $I_3$.

In the illustration 82 the second three-dimensional anatomical model $M_2$ is projected onto the perioperative image $I_3$.

Preferably, a function of opacity is applied to the 2D perioperative image, making it possible to improve the simultaneous visualisation of the endovascular tools and of the three-dimensional anatomical model projected.

In addition, the invention makes it possible to improve guiding and navigation in vascular structures by displaying additional information obtained from the second three-dimensional anatomical model which is representative of the deformations of the vascular structures at the time of the intervention.

Figure 7:
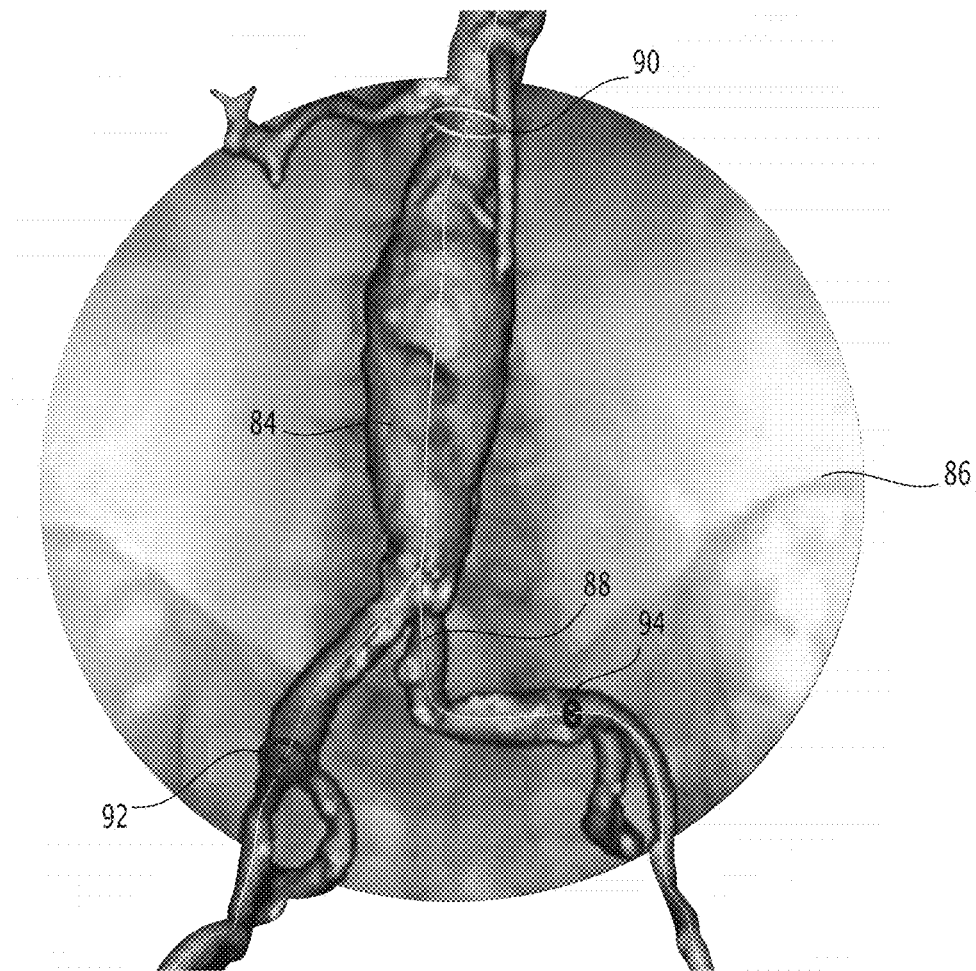
FIG. 7 is an example of an enriched display comprising an anatomical model after application of the elastic transformation.

FIG. 7 shows such a three-dimensional anatomical model after deformation 84 displayed in superposition of a perioperative 2D image 86. The display is as such enriched with additional information in augmented reality.

The display also contains an aortic central line 88 obtained by calculation, as well as anatomical markers 90, 92, 94 superimposed at anatomical points of interest, namely the ostium 90, and the points of departure of the right 92 and left 94 of the iliac artery.

All of the anatomical markers were extracted beforehand from the first three-dimensional anatomical model, and are visual indications that make it possible to enrich all of the information supplied to the practitioner.

Advantageously, a use of the deformed three-dimensional anatomical model supplied by the invention is the monitoring of the inserted endovascular tool, making it possible to provide a spatial location of the tool in real time. This monitoring is based on opaque radio markers, an infrared system or an electromagnetic system.

According to another alternative, the monitoring of tools is carried out manually by selection of the endovascular tool monitored in the displayed image.

The invention has applications in various procedures that require endovascular interventions, in particular the treatment of aneurysms, vascular trauma or arteriosclerosis.

Although the present disclosure has been described with reference to one or more examples, workers skilled in the art will recognize that changes may be made in form and detail without departing from the scope of the disclosure and/or the appended claims.

The invention claimed is:

1. A method for helping to guide an endovascular tool in vascular structures, wherein the method comprises acts of:
   during an initial planning phase,
      obtaining and memorising a preoperative three-dimensional image comprising a target vascular structure of a patient,
      determining a first three-dimensional anatomical model specific to the patient from the three-dimensional image acquired, with this first three-dimensional anatomical model being located in the same spatial reference as the three-dimensional image, and
   during an intervention phase,
      acquiring one or several perioperative two-dimensional images comprising the target vascular structure of the patient, opacified or not,
      estimating a rigid transformation between the preoperative three-dimensional image and the perioperative two-dimensional images,
      estimating an elastic transformation between said three-dimensional image and the two-dimensional images according to the rigid transformation and of a simulation of vascular deformations induced by introducing the tool into the target vascular structure,
      applying a final transformation, a combination of the rigid transformation and of the elastic transformation, to the first three-dimensional anatomical model specific to the patient in order to obtain a second three-dimensional model specific to the patient, and
      displaying said second three-dimensional model specific to the patient as superposition on the two-dimensional images acquired.

2. The method according to claim 1, wherein the act of estimating an elastic transformation comprises modelling of the vascular structures of the patient from the preoperative three-dimensional image acquired.

3. The method according to claim 1, wherein the act of estimating an elastic transformation comprises constructing biomechanical interaction model between the vascular structures and the endovascular tool.

4. The method according to claim 3, comprising simulation of the interaction between the endovascular tool and the target vascular structure carried out by a finite element analysis method.

5. The method according to claim 1, wherein the estimating of the elastic transformation comprises an additional act of correlation that uses said perioperative two-dimensional images.

6. The method according to claim 5, wherein the act of correction comprises a projection of simulated positions of the endovascular tool on at least one perioperative two-dimensional image taken after the actual introduction of the endovascular tool, and a quantification of the difference between said simulated positions and actual positions of the endovascular tool.

7. The method according to claim 6, further comprising an act of recalibration between said simulated positions and said actual positions.

8. The method according to claim 1, wherein the first three-dimensional anatomical model specific to the patient is represented by a structure among a volume, a mesh of points, a set of contours and a set of anatomical markers.

9. The method according to claim 1, wherein the estimating of a rigid transformation is carried out by automatic, semi-automatic or manual recalibration, between the preoperative three-dimensional image and at least one perioperative two-dimensional image.

10. A system for helping to guide an endovascular tool in vascular structures, comprising:
   an imaging device to acquire two-dimensional images of portions of a body of a patient;
   a programmable device; and
   a viewing unit,
   wherein the programmable device is configured to:
   during an initial planning phase,
      obtaining and memorising a preoperative three-dimensional image comprising a target vascular structure of a patient,
      determining a first three-dimensional anatomical model specific to the patient from the three-dimensional image acquired, with this first three-dimensional anatomical model being located in the same spatial reference as the three-dimensional image,
   during an intervention phase,
      acquire one or several perioperative two-dimensional images comprising the target vascular structure of the patient, opacified or not,
      estimate a rigid transformation between the preoperative three-dimensional image and the perioperative two-dimensional images,
      estimate an elastic transformation between said three-dimensional image and the two-dimensional images according to the rigid transformation and a simulation of vascular deformations induced by introducing the tool into the target vascular structure,
      apply a combination of the rigid transformation and of the elastic transformation to the first three-dimensional anatomical model specific to the patient in order to obtain a second three-dimensional model specific to the patient, and
      display on the viewing unit said second three-dimensional model specific to the patient in superposition on the two-dimensional images acquired.

11. A non-transitory computer-readable medium comprising a computer program stored thereon comprising instructions for implementing acts of a method for helping to guide an endovascular tool in vascular structures during execution of the program by a processor of a programmable device, wherein the method comprises:
   during an initial planning phase,
      obtaining and memorising a preoperative three-dimensional image comprising a target vascular structure of a patient,
      determining a first three-dimensional anatomical model specific to the patient from the three-dimensional image acquired, with this first three-dimensional anatomical model being located in the same spatial reference as the three-dimensional image, and
   during an intervention phase,
      acquiring one or several perioperative two-dimensional images comprising the target vascular structure of the patient, opacified or not,
      estimating a rigid transformation between the preoperative three-dimensional image and the perioperative two-dimensional images,
      estimating an elastic transformation between said three-dimensional image and the two-dimensional images according to the rigid transformation and of a simulation of vascular deformations induced by introducing the tool into the target vascular structure,
      applying a final transformation, a combination of the rigid transformation and of the elastic transformation, to the first three-dimensional anatomical model specific to the patient in order to obtain a second three-dimensional model specific to the patient, and
      displaying said second three-dimensional model specific to the patient as superposition on the two-dimensional images acquired.

* * * * *